(12) United States Patent
Liu et al.

(10) Patent No.: US 11,964,149 B2
(45) Date of Patent: Apr. 23, 2024

(54) FACIAL BEAUTIFYING AND CARE APPARATUS

(71) Applicants: BIBOTING INTERNATIONAL CO., LTD., Taoyuan (TW); Po-Chang Liu, Taoyuan (TW)

(72) Inventors: Po-Chang Liu, Taoyuan (TW); Pei-En Lee, New Taipei (TW)

(73) Assignees: BIBOTING INTERNATIONAL CO., LTD., Taoyuan (TW); Po-Chang Liu, Taoyuan (TW)

( * ) Notice: Subject to any disclaimer, the term of this patent is extended or adjusted under 35 U.S.C. 154(b) by 0 days.

(21) Appl. No.: 18/123,349

(22) Filed: Mar. 20, 2023

(65) Prior Publication Data
US 2023/0225928 A1 Jul. 20, 2023

Related U.S. Application Data

(63) Continuation of application No. 16/942,804, filed on Jul. 30, 2020, now abandoned.

(51) Int. Cl.
*A61N 1/32* (2006.01)
*A61H 9/00* (2006.01)
(Continued)

(52) U.S. Cl.
CPC ........... *A61N 1/328* (2013.01); *A61H 9/0057* (2013.01); *A61N 1/0452* (2013.01); *A61N 1/44* (2013.01);
(Continued)

(58) Field of Classification Search
CPC ........ A61N 1/328; A61N 1/0452; A61N 1/44; A61N 5/0616; A61N 7/00;
(Continued)

(56) References Cited

U.S. PATENT DOCUMENTS 5,800,485 A * 9/1998 Trop .......................... A61F 7/12
607/105
2003/0187462 A1* 10/2003 Chang .................... A61B 17/54
606/131
(Continued)

*Primary Examiner* — Hien N Nguyen
(74) *Attorney, Agent, or Firm* — Chun-Ming Shih; HDLS IPR SERVICES

(57) ABSTRACT

A facial beautifying and care apparatus includes a beauty bar (1) having an air supply passage (A), a negative pressure connecting hole (132), a conductive suction nozzle (15) and a first connection port (134); an EMS generation module (20) inside the beauty bar (1) electrically connected to the first connection port (134); an external negative pressure unit (6) separated from the beauty bar (1) and having a negative pressure driving control module (62) and a second connection port (637); the negative pressure driving control module (62) having an air supply tube assembly (66) with a negative pressure communicating hole (661); a communicating tube (7) communicating with the negative pressure connecting hole (132) and the negative pressure communicating hole (661); a conductive wire (8) connected to the first connecting port (134) and the second connecting port (637). Accordingly, the effects of facial skin firming, cleaning, beautifying and caring are achieved.

13 Claims, 6 Drawing Sheets

(51) Int. Cl.
    *A61H 23/02*      (2006.01)
    *A61N 1/04*      (2006.01)
    *A61N 1/44*      (2006.01)
    *A61N 5/06*      (2006.01)
    *A61N 7/00*      (2006.01)
    *F21V 11/00*      (2015.01)
    *F21V 33/00*      (2006.01)
    *F21Y 115/10*      (2016.01)
    *H01J 27/02*      (2006.01)

(52) U.S. Cl.
    CPC ............ *A61N 5/0616* (2013.01); *A61N 7/00* (2013.01); *F21V 11/00* (2013.01); *F21V 33/004* (2013.01); *H01J 27/028* (2013.01); *A61H 23/0245* (2013.01); *A61H 2201/10* (2013.01); *A61H 2201/1238* (2013.01); *A61H 2205/022* (2013.01); *A61N 2005/0644* (2013.01); *A61N 2005/0652* (2013.01); *A61N 2005/0663* (2013.01); *A61N 2007/0034* (2013.01); *F21Y 2115/10* (2016.08)

(58) Field of Classification Search
    CPC .... A61N 2005/0644; A61N 2005/0652; A61N 2005/0663; A61N 2007/0034; A61N 2005/0651; A61H 9/0057; A61H 23/0245; A61H 2201/10; A61H 2201/1238; A61H 2205/022; A61H 2201/0188; A61H 2201/5025; F21V 11/00; F21V 33/004; H01J 27/028; F21Y 2115/10; H01T 23/00
    See application file for complete search history.

(56) References Cited

U.S. PATENT DOCUMENTS

2009/0192442 A1\*    7/2009    Ignon .................... A61B 17/32
                                                                            604/22
2017/0043070 A1\*    2/2017    Locke .................... A61M 1/64

\* cited by examiner

FACIAL BEAUTIFYING AND CARE APPARATUS

CROSS-REFERENCE TO RELATED APPLICATION

This application is a continuing application of U.S. patent application Ser. No. 16/942,804, filed on Jul. 30, 2020, and entitled "FACIAL BEAUTIFYING AND CARE APPARATUS". The entire disclosures of the above application are all incorporated herein by reference.

BACKGROUND OF THE INVENTION

Field of the Invention

The technical field relates to a beautifying and care apparatus and technology, and in particular, to a facial beautifying and care apparatus.

Description of Related Art

Due to external air pollution and stress from work, facial skin can become mottled and loose. Despite the use of high-end and expensive skin care products, without proper care, they may not be properly absorbed by facial skin. Accordingly, those who care about their facial beauty usually receive their aesthetic care at beauty salons. However, most of the beautifying machines used at aesthetic centers or beauty salons are bulky and require a large space for placement and installation. Furthermore, such beautifying machines require machine operators to operate onsite, and they are extremely inconvenient for personal use. Moreover, for a person who plans to receive aesthetic care, it is necessary to not only schedule a time and make a reservation with aesthetic centers or beauty salons, but to also wait patiently for a long period of time. Consequently, such a process is time and labor consuming, and it is not possible own a beautifying machine and complete the process at home through a DIY (Do-It-Yourself) method.

Manufacturers have developed relevant products for the aforementioned deficiencies, and one of the most commonly seen products is the beauty bar with a vibration function, which mainly comprises a rod and a vibrator installed inside the bar, such that the vibrator is able to drive the rod to generate a corresponding vibration effect. When the rod contacts the facial skin, it is able to massage and relieve stress on the facial skin.

Although the currently available beautifying and care devices can provide a level of massage and stress relief, during the actual process of use, the facial skin and its internal tissues are unable to obtain sufficient movement, which renders the current devices relatively ineffective at providing skin revitalization and blood circulation. In addition, most of the currently available beautifying and care devices are single function only, and users are required to make different purchases according to their different needs, such that the purchase cost of users is significantly increased. Accordingly, there is a need for a beautifying and care device capable of satisfying the current market demands.

In view of above, the inventor seeks to improve and overcome the aforementioned drawbacks associated with the currently existing technology after years of research and development along with the utilization of academic theories in order to achieve a reasonable design of the present invention capable of effectively overcoming the aforementioned drawbacks.

SUMMARY OF THE INVENTION

An objective of the present invention is to provide a facial beautifying and care apparatus, capable of generating the beautifying and care effects of firming and cleaning of skin and generating electro muscle simulation while facilitating the operation of the apparatus.

To achieve the aforementioned objective, the present invention provides a facial beautifying and care apparatus, comprising: a beauty bar, an electro muscle simulation generation module, an external negative pressure unit, a communicating tube and a conductive wire. The beauty bar includes an air supply passage arranged therein, and the beauty bar includes a negative pressure connecting hole and a conductive suction nozzle communicating with the air supply passage and arranged at two ends thereof respectively. The negative pressure connecting hole includes a first connection port arranged at a lateral side thereof. The electro muscle simulation generation module is arranged inside the beauty bar and is electrically connected to the first connection port. The external negative pressure unit is arranged separately from the beauty bar. The external negative pressure unit comprises a housing and a negative pressure driving control module installed inside the housing. The negative pressure driving control module comprises an air supply tube assembly, and the air supply tube assembly includes a negative pressure communicating hole arranged on the housing. The external negative pressure unit further comprises a second connection port. The connecting tube includes two ends connected to the negative pressure connecting hole and the negative pressure communicating hole. The conductive wire includes two ends connected to the first connecting port and the second connection port. In addition, through an operation of the negative pressure driving control module, the conductive suction nozzle is able to generate negative pressure suction on facial skin, and a current flows outward via the electro muscle simulation generation module, thereby allowing the conductive suction nozzle to simulate the facial skin to generate adenosine tri-phosphate. wherein the electro muscle simulation generation module comprises a control assembly and an electro muscle simulation transmission assembly, the control assembly is electrically connected to the first connection port, the control assembly comprises a circuit board and a first switch button installed on the circuit board in order to turn on or off the electro muscle simulation transmission assembly via a control on the first switch button. wherein the electro muscle simulation transmission module assembly comprises a wire, the conductive suction nozzle comprises a connector and a connector cap connected thereto, the connector includes a second connecting tube, one end of the wire is electrically connected to the control assembly, and another end of the wire is attached to the second connecting tube.

The present invention is also able to achieve the following effects. With the installation of a ultrasonic generation module, through the high frequency vibration generated by a piezoelectric plate assembly, high frequency vibrations can be transmitted from the conductive suction nozzle to the facial skin in order to facilitate the cleaning of skin pores and removal of acne, and is also able to promote the skin absorption of care products. With the anti-false touch assembly, a user is required to use their hand to touch the capacitive sensing press zone of the beauty bar, and the conductive suction nozzle is required to contact the facial skin in order to activate the electro muscle stimulation function such that an accidental activation can be prevented and the safety can be enhanced. With the light wave generation module, when light is projected onto the facial skin, it is able to stimulate the blood circulation, increasing the elasticity and luster of skin. With the arrangement of the conical light cups corresponding to the light emitting diodes, the light projection scope of the light emitting diodes is of greater uniformity. Furthermore, with the negative ion generation module and the output of the negative ions from the negative ion emission hole at the front, it is able to enhance the blood circulation of the facial skin.

DETAILED DESCRIPTION OF THE INVENTION

Figure 1:
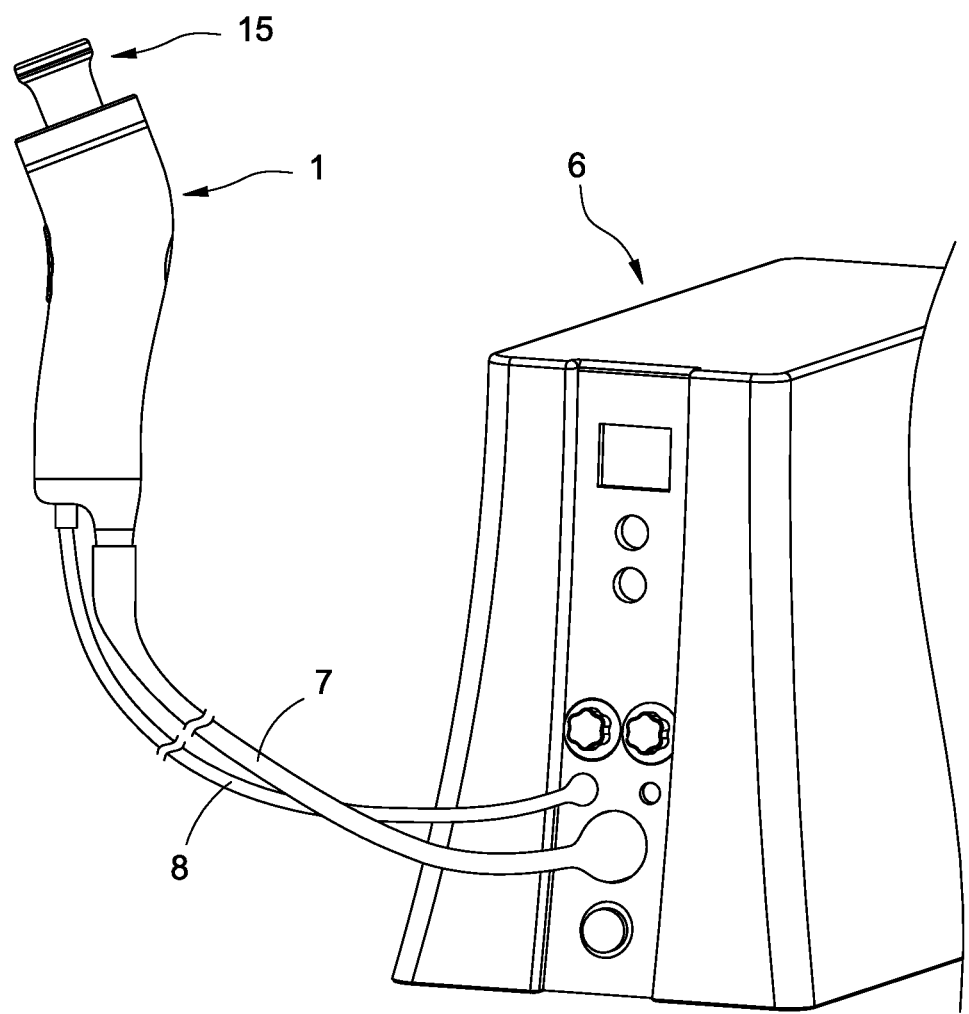
FIG. 1 is an assembly perspective view of the facial beautifying and care apparatus of the present invention.
Figure 2:
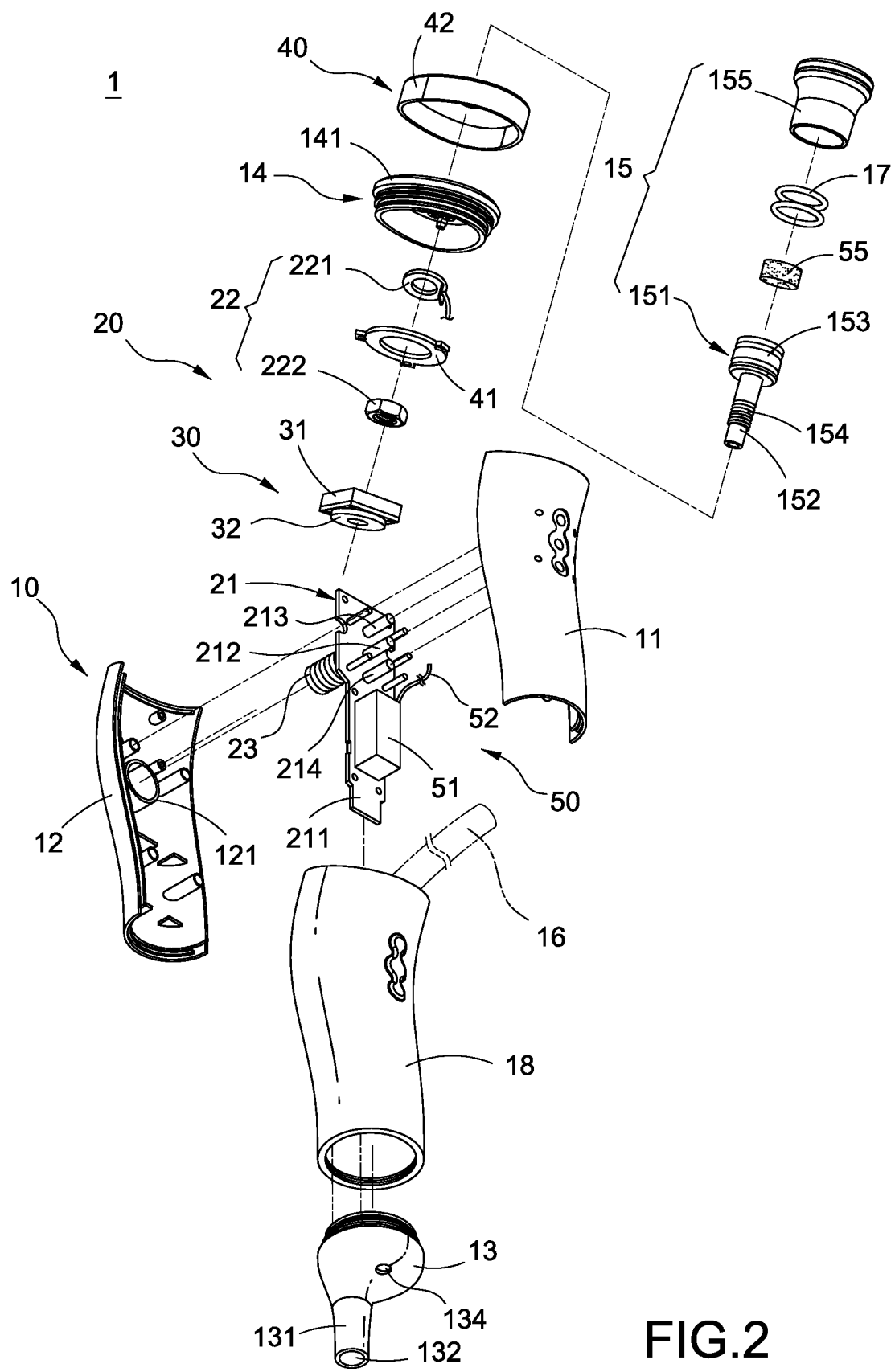
FIG. 2 is a perspective exploded view of the beauty bar of the present invention.
Figure 3:
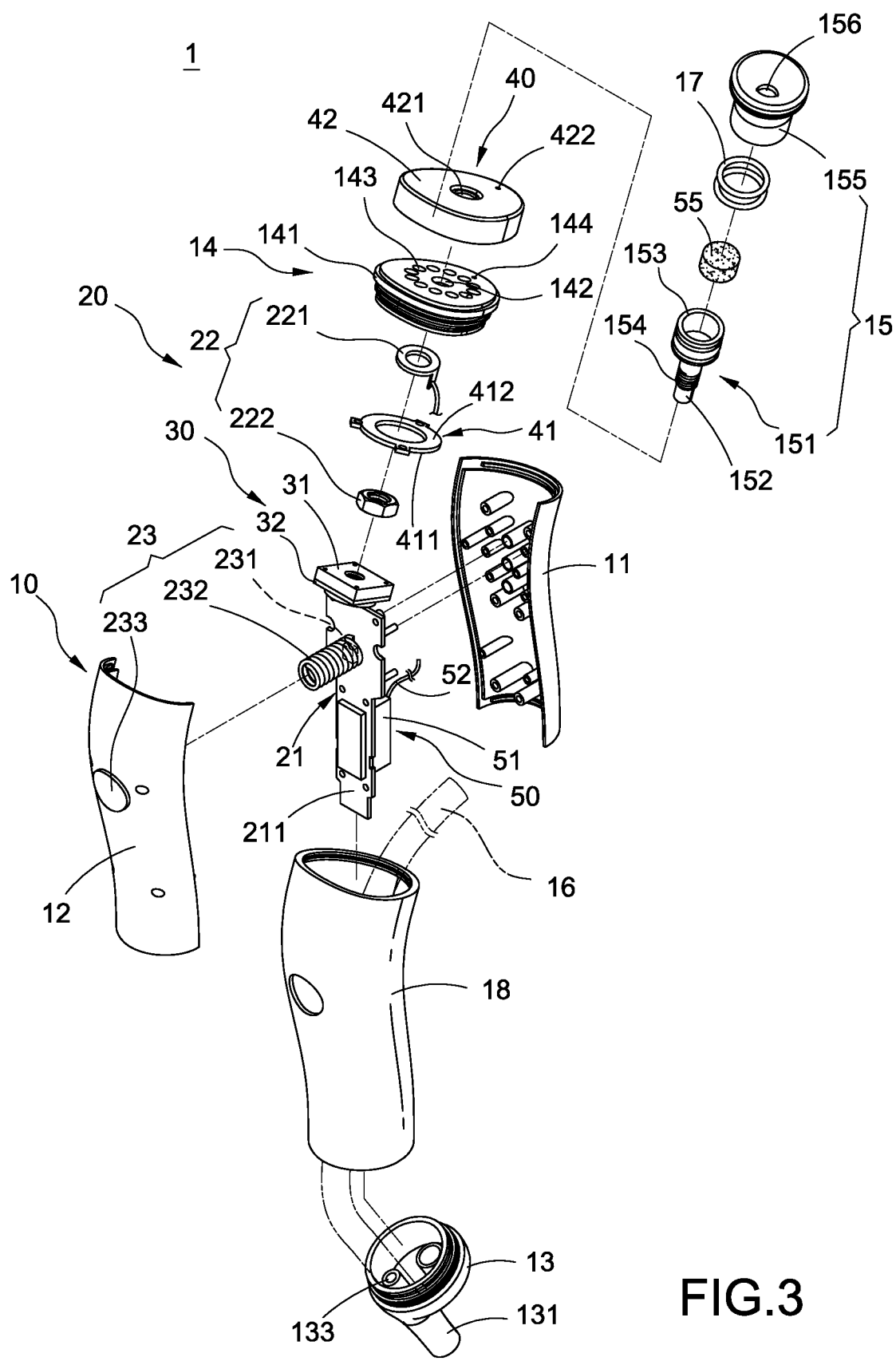
FIG. 3 is a perspective exploded view of the beauty bar of the present invention viewed from another angle.
Figure 4:
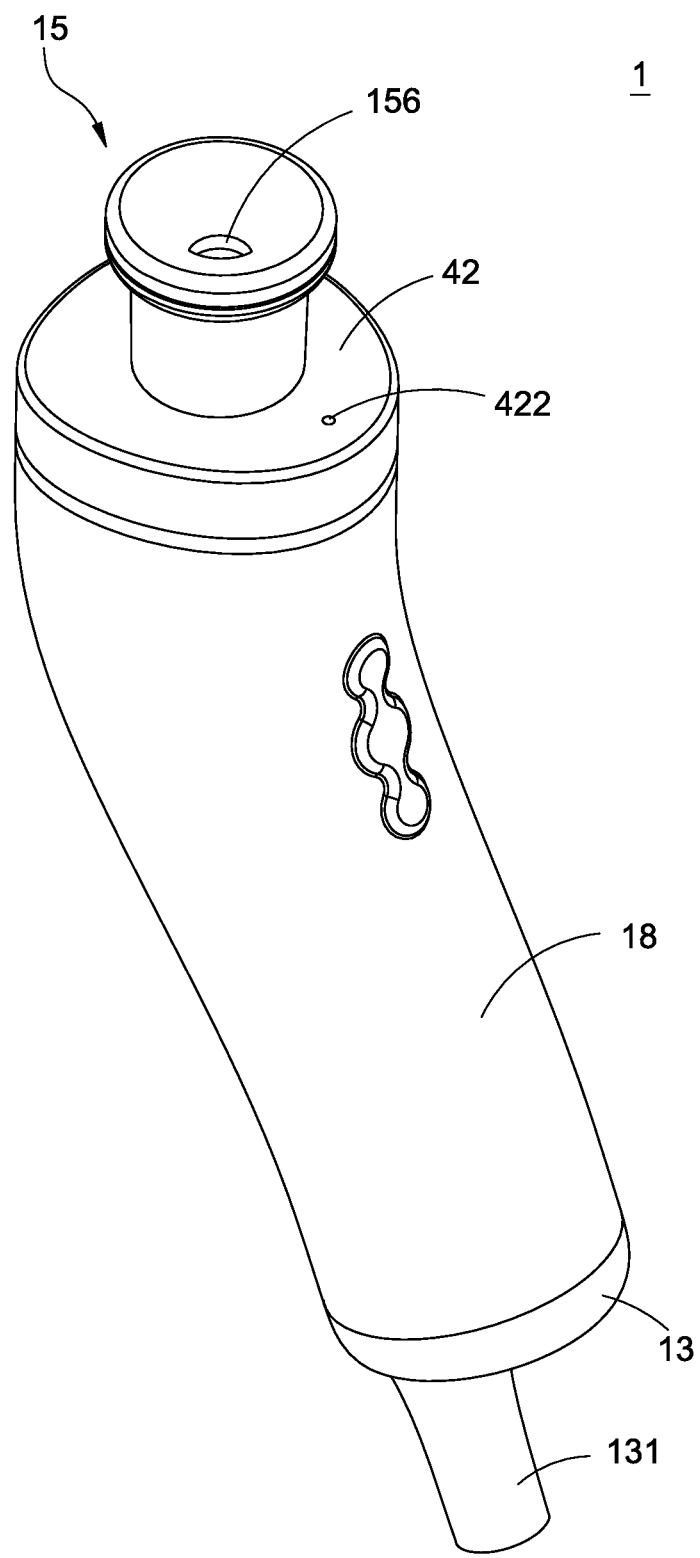
FIG. 4 is an assembly appearance view of the beauty bar of the present invention.
Figure 5:
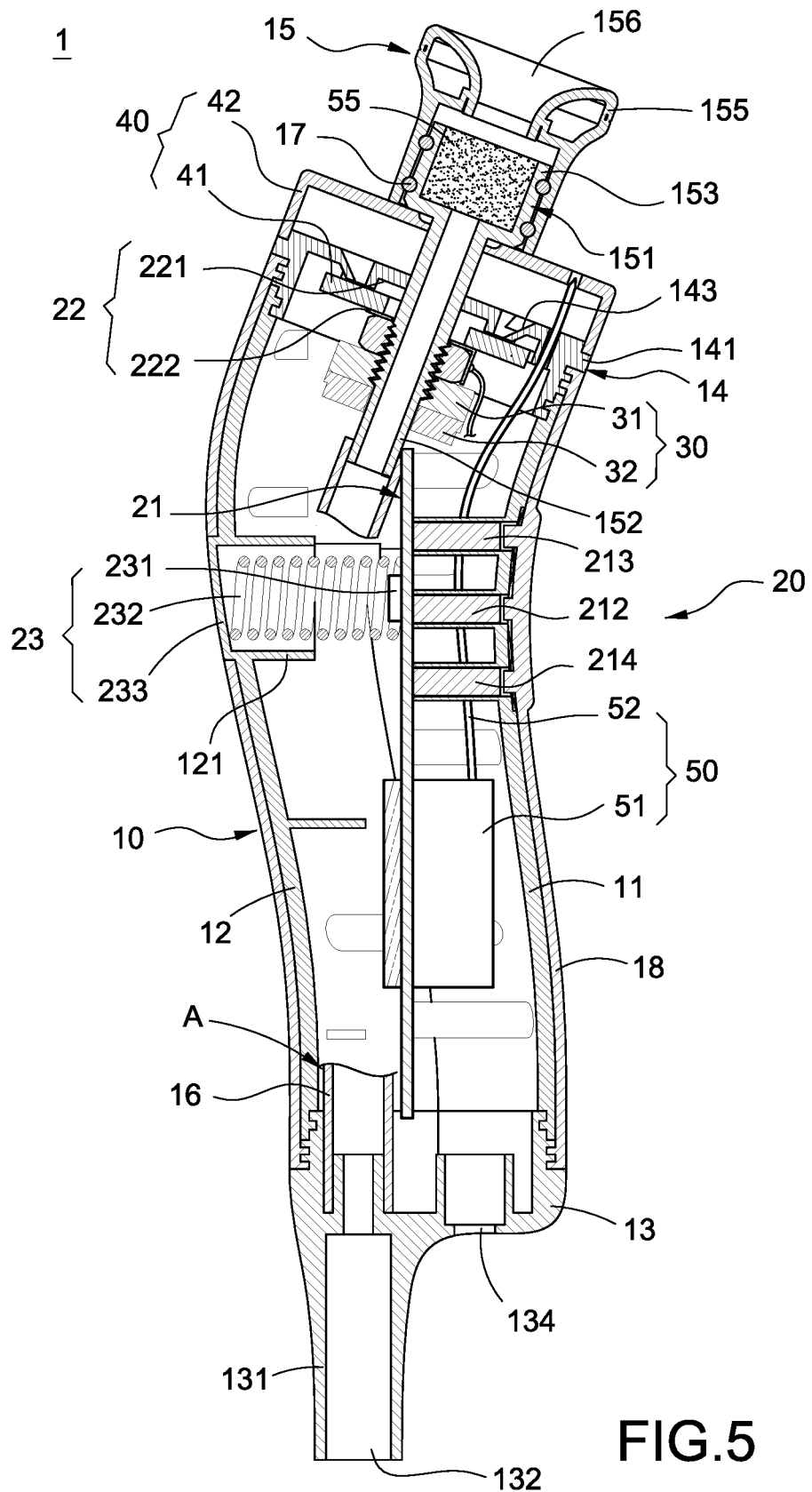
FIG. 5 is an assembly cross sectional view of the beauty bar of the present invention.

The following provides a detailed technical content of the present invention along with the accompanied drawings. However, it shall be understood that the accompanied drawings are provided for reference and illustration purposes only, and shall not be used to limit the scope of the present invention.

As shown in FIG. 1 to FIG. 7, the present invention provides a facial beautifying and care apparatus, mainly comprising a beauty bar 1, an electro muscle simulation generation module 20, an external negative pressure unit 6, a communicating tube 7 and a conductive wire 8. The beauty bar 1 and the external negative pressure unit 6 are arranged separately from each other, i.e. independent from each other, and it is necessary to use the communicating tube 7 and the conductive wire 8 to achieve the connection between the beauty bar 1 and the external negative pressure unit 6.

First, please refer to FIG. 2 to FIG. 5. The beauty bar 1 mainly comprises a bar member 10 with a generally curved cylindrical body. In an exemplary embodiment of the present invention, the bar member 10 mainly comprises a front housing 11, a rear housing 12, a lower cap 13, an upper cap 14 and a conductive suction nozzle 15. The front housing 11, the rear housing 12, the lower cap 13 and the upper cap 14 are made of a material with excellent insulation, such as plastic. The front housing 11 is assembled onto the rear housing 12 with fasteners such as screws for fastening. The lower cap 13 is assembled onto a lower end position of the front housing 11 and the rear housing 12. The upper cap 14 is assembled onto an upper end position of the front housing 11 and the rear housing 12. The conductive suction nozzle 15 is arranged to penetrate into a center area of the upper cap 14.

One side of the lower cap 13 includes an extension tube 131 formed thereon, and a negative pressure connecting hole 132 is formed at a center of the extension tube 131. A first connecting tube 133 extends from a lower portion of the extension tube 131 correspondingly, and the negative pressure connecting hole 132 communicates with the first connecting tube 133. In addition, the negative pressure connecting hole 132 of the lower cap 13 includes a first connection port 134 arranged at a lateral side thereof. In an exemplary embodiment of the present invention, the first connection port 134 is a conductive connecting hole, but the present invention is not limited to such a configuration only.

The upper cap 14 mainly comprises a shield disk 141, and a center of the shield disk 141 includes a receiving hole 142. The conductive suction nozzle 15 mainly comprises a connector 151 and a connector cap 155. The connector 151 and the connector cap 155 are made of a material with excellent electrical conductivity, such as metal. The connector 151 includes a second connecting tube 152 and a hollow cylinder 153 extended from and communicating with the second connecting tube 152. The second connecting tube 152 penetrates into the receiving hole 142, and the hollow cylinder 153 is formed at an exterior of the shield disk 141. The connector cap 155 is mounted onto the hollow cylinder 153, and a center of the connector cap 155 includes an intake opening 156 communicating with the hollow cylinder 153 and the second connecting tube 152. As a connecting tube 16 respectively communicates with the first connecting tuber 133 and the second connecting tube 152, an air supply passage A is formed inside the bar member 10.

Furthermore, in an exemplary embodiment of the present invention, the bar member 10 further comprises a waterproof gasket 17, and the waterproof gasket 17 is clamped between the hollow cylinder 153 and the connector cap 155. The waterproof gasket 17 can be made of a silicon material in order to effectively prevent air leakage.

Moreover, in an exemplary embodiment of the present invention, the bar member 10 further comprises a silicon cover 18, which is used to enclose and cover onto an exterior of the front housing 11 and the rear housing 12, and is connected to the lower cap 13 and the upper cap 14 in order to achieve an effective waterproof effect for the beauty bar 1.

The electro muscle simulation (EMS) generation module 20 is arranged inside the beauty bar 1 and is electrically connected to the first connection port 134. The current value of the electro muscle simulation generation module 20 is typically between 1~400 μA, and mainly comprises a control assembly 21 and an electro muscle stimulation transmission assembly 22. The control assembly 21 is electrically connected to the first connection port 134, and mainly comprises a circuit board 211 and a first switch button 212 installed on the circuit board 211. A portion of the first switch button 212 is exposed at an exterior of the front housing 11, and the electro muscle simulation transmission assembly 22 is turned on or off via the control performed on the first switch button 212. In an exemplary embodiment of the present invention, the electro muscle simulation transmission assembly 22 mainly comprises a wire 221 and a fixation member 222. In an exemplary embodiment, the fixation member 222 is a nut, and a fastening portion 154 is formed at an outer circumferential edge of the second connecting tube 152. One end of the wire 221 is electrically connected to the control assembly 21 and another end of the wire 221 is attached to the second connecting tube 152 and is fastened corresponding to the fastening portion 154 via the fixation member 222, thereby allowing the electro muscle stimulation to be transmitted to the facial skin via the conductive suction nozzle 15. In addition, such electro muscle stimulation is able to stimulate the dermis to promote the generation of Adenosine Tri-phosphate (ATP), formed by adenosine and tri-phosphate, with the chemical formula of $C_{10}H_{16}N_5O_{13}P_3$, the structural formula of $C_{10}H_8N_4O_2NH_2(OH)_2(PO_3H)_3H$, and the molecular weight of 507.184.

Furthermore, in an exemplary embodiment of the present invention, the electro muscle stimulation generation module 20 further comprises an anti-false touch assembly 23, which can be a capacitive touch button sensor and mainly comprises a capacitive sensing switch 231, a conductive spring 232 and a sensing portion 233. The capacitive sensing switch 231 is arranged on a circuit board 211 of the control assembly 21. The conductive spring 232 is supported inside a cylindrical column 121 of the rear housing 12, and one end of the conductive spring 232 is arranged corresponding to the capacitive sensing switch 231. The sensing portion 233 is formed on the rear housing 12 and is arranged corresponding to another end of the conductive spring 232. Accordingly, a user is required to use his or her hand to touch the location of the sensing portion 233 on the rear housing 12 and the facial skin is required to contact the conductive suction nozzle 15 in order to activate the electro muscle stimulation function such that the situation of accidental activation can be effectively prevented, thereby enhancing safety thereof.

Figure 6:
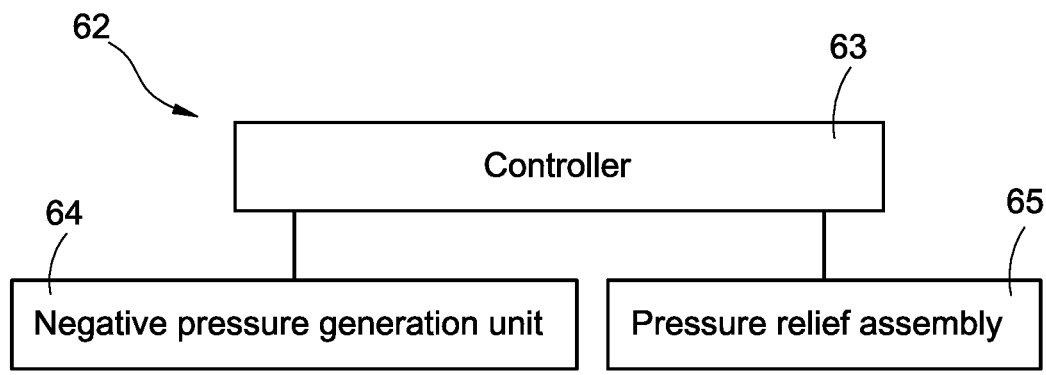
FIG. 6 is a perspective appearance view of the eternal negative pressure unit of the present invention.
Figure 7:
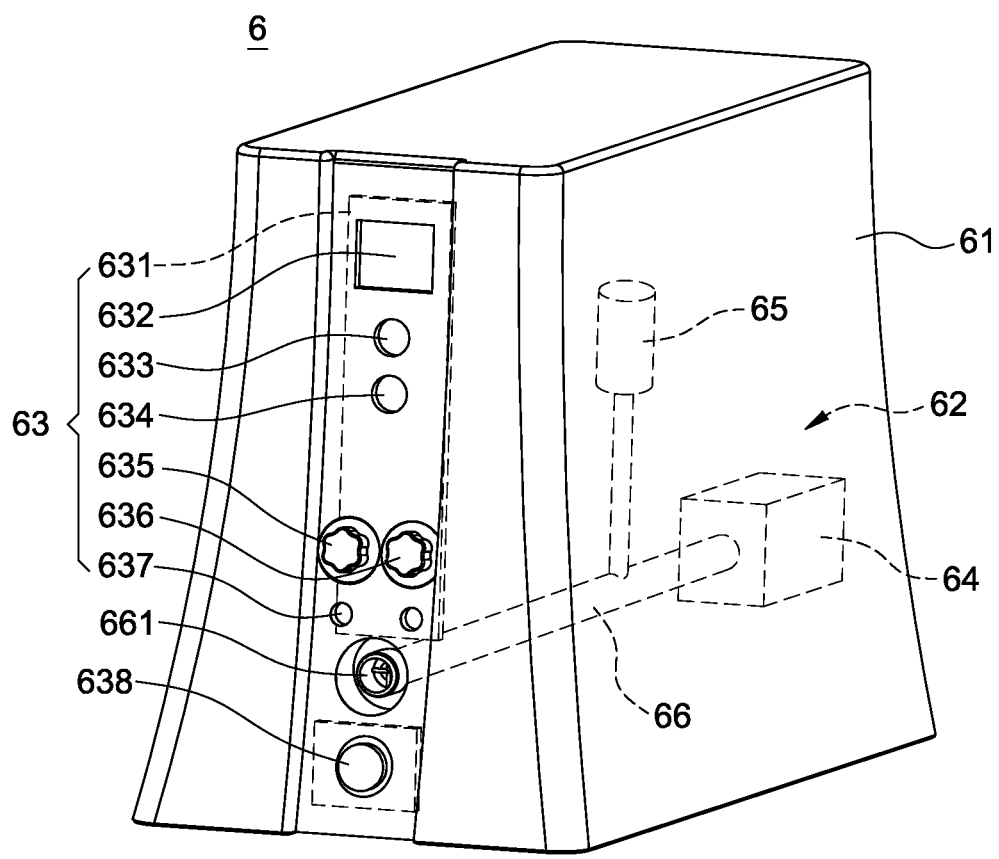
FIG. 7 is a block diagram of the negative pressure driving control module of the present invention.

Please refer to FIG. 6 and FIG. 7. The external negative pressure unit 6 mainly comprises a housing 61 and a negative pressure driving control module 62 arranged inside the housing 61. The negative pressure driving control module 62 mainly comprises a controller 63, a negative pressure generation assembly 64, a pressure relief assembly 65 and an air supply tube assembly 66. The controller 63 comprises a main circuit board 631, and the main circuit board 631 includes a display panel 632, a continuous suction button 633, an intermittent suction release button 634, a negative pressure time control button 635, a pressure relief time control button 636 and two second connection ports 637 disposed thereon; wherein the second connection port 637 can be a direct current electrical connecting hole, and is electrically connected to the controller 63 via a power button 638. The negative pressure generation assembly 64 and the pressure relief assembly 65 are electrically connected to the controller 63. The air supply tube assembly 66 communicates with the negative pressure generation assembly 64 and the pressure relief assembly 65. In addition, the air supply tube assembly 66 includes a negative pressure communicating hole 661 secured onto the housing 61. Furthermore, the negative pressure generation assembly 64 mainly comprises a vacuum pump and a motor (not shown in the drawings), and is provided to generate a negative pressure force in order to allow the conductive suction nozzle 15 of the beauty bar 1 to perform suction on facial skin. During the normal use of the apparatus, the maximum negative pressure force is limited to be within −46.7 kPa (−3500 mHg).

Please refer to FIG. 1 again. The two ends of the communicating tube 7 communicate with the negative pressure connecting hole 132 and the negative pressure communicating hole 661 respectively, such that through an operation of the negative pressure driving control module 62, the conductive suction nozzle 15 of the beauty bar 1 is able to generate an alternating suction-release rhythmic massage of negative pressure massaging and negative pressure relief. The conductive wire 8 is electrically connected to the beauty bar 1 and the external negative pressure unit 6. To be more specific, the two ends of the conductive wire 8 are electrically connected to the first connection port 134 and the second connection port 637 respectively.

It shall be noted that the combination of the external negative pressure unit 6 and the beauty bar 1 with the adjustment of the vacuum level and the suction-release frequency is able to achieve the effect of skin firming and cleaning as well as the removal of acne and dirt etc.

During the use of the apparatus, it is able to perform suction massages with negative pressure on the facial skin and rhythmic suction-release alternating massages with the negative pressure relief. After the conductive suction nozzle 15 contacts the skin, the vacuum pump of the negative pressure generation unit 64 activates and a negative pressure force is generated at the intake opening 156 in order to suck the skin to upward. When the negative pressure is stopped, the suction on the skin is stopped. Next, with the operation of the pressure relief assembly 65, when the air enters into the air supply passage A via the air supply tube assembly 66, the negative pressure force is released such that the negative pressure is reduced, and the skin is able to return to its original state, and such actions can be repeated. During such time, the electro muscle stimulation module 20 can be turned on or off at any time. As a microcurrent is outputted from the conductive suction nozzle, it is able to simulate the muscle massage in order to allow the muscle to restore its elasticity, and the current is also able to simulate the dermis to promote cells to generate a greater amount of Adenosine Tri-phosphate (ATP). In addition, since ATP is an essential substance for the generation of collagen, as the microcurrent massages the face, collagen can be generated swiftly and facial lines become more prominent, thereby achieving the effect of facial skin firming. Such a method is also able to allow the partial adipose layer to receive sufficient exercise. Consequently, the basal metabolism of human body is increased, achieving the effect of fat reduction and removal.

Furthermore, according to an exemplary embodiment of the present invention, the apparatus further comprises an ultrasonic generation module 30, which is arranged inside the beauty bar 1 and is electrically connected to the control assembly 21, mainly comprising a fixation plate 31 and a piezoelectric plate assembly 32 connected to the fixation plate 31. The fixation plate 31 and the piezoelectric plate assembly 32 are mounted onto the second connecting tube 152. The piezoelectric plate assembly 32 transmits a high frequency vibration in order to allow the conductive suction nozzle 15 to promote skin pore cleaning and skin absorption of care products. The vibration frequency of the piezoelectric plate assembly 32 is typically between 1~3 MHz. The control assembly 21 further comprises a second switch button 213 installed on the circuit board 211. A portion of the second switch button 213 is exposed at an exterior of the front housing 11, and the actuation of the ultrasonic generation module 30 can be turned on or off via the operation on the second switch button 213.

It shall be noted that since the effective ingredients in skin care products are mostly composed of organic large molecules, under their natural state, such molecules cannot penetrate through the dermis of the facial skin; in other words, during the application of a care product with the use of fingers, the nutrient elements stay at the surface of the skin without being absorbed by the deeper layer of the skin. An ultrasonic generation module 30 in conjunction with the conductive suction nozzle 15, through the characteristics of high frequency vibration and strong penetrating capability, is able to generate high-energy exercise on the skin. As a result, it is able to not only increase the tissue metabolism to achieve the softening of tissue and an enhanced firming effect but can also promote the cleaning of skin pores and removal of acne.

In addition, according to an exemplary embodiment of the present invention, the apparatus further comprises a light wave generation module 40, mainly comprising a light emitting assembly 41 and a light shield 42. The light emitting assembly 41 is arranged inside the beauty bar 1 and is electrically connected to the control assembly 21. The light shield 42 is covered onto an exterior of the shield disk 141, and the shield disk 141 further includes a plurality of conical light cups 143. Each of the conical light cups 143 is arranged spaced apart from each other and configured to surround an outer circumference of the receiving hole 142. The light emitting assembly 41 is electrically connected to the control assembly 21 and mainly comprises a substrate 411 and a plurality of light emitting diodes 412 disposed on the substrate 411. The light emitting assembly 41 is arranged inside the upper cap 14, and each of the light emitting diodes 412 is arranged corresponding to the location of each conical light cups 143. The light shield 42 is made of a light transmissive material, and it is covered onto an exterior of the upper cap 14. The control assembly 21 further comprises a third switch button 214 installed on the circuit board 211. A portion area of the third switch button 214 is exposed at an exterior of the front housing 11, and the actuation of the light wave generation module 40 is turned on or off via the operation of the third switch button 214.

It shall be noted that a light emitting diode (LED) can be divided into the three types of light colors of red, yellow and blue. With the utilization of different functions on the muscle tissues, after the light of a specific wavelength is absorbed by the skin, it is transformed into internal energy by the cells, thereby promoting the cell metabolism and synthesis, improving facial skin conditions. A red LED is able to increase the cell vitality, increase skin elasticity, repair skin and mitigate skin aging, such that skin can be restored with vitality. A blue LED is able to achieve the effects of sterilization and anti-inflammation, suppress pimples and acne, repair skin surface roughness and regulate balance between oil and water. A yellow LED is able to accelerate blood circulation and activate cells, remove dull spots and brighten skin color.

Furthermore, according to an exemplary embodiment of the present invention, the apparatus further comprises a negative ion generation module 50, arranged inside the beauty bar 1 and electrically connected to the control assembly 21. In addition, the negative ion generation module 50 mainly comprises a negative ion generator 51 and a negative ion wire 52 connected to the negative ion generator 51. The shield disk 141 includes a negative ion output hole 144 formed thereon, and the light shield 42 includes a negative ion emission hole 421 arranged corresponding to the negative ion output hole 144; wherein the negative ion wire 52 penetrates into the negative ion output hole 144 and extends into the negative ion emission hole 421. The negative ions generated by the negative ion generator 51 are emitted from the rear end of the negative ion wire 52, which is able to enhance the effect of skin blood circulation, and the activation of the negative ion generation module 50 can be operated immediately after the power is turned on.

Moreover, according to an exemplary embodiment of the present invention, the apparatus further comprises a filter member 55, arranged inside a hollow cylinder 153 of the conductive suction nozzle 15. In an exemplary embodiment, the filter member is a filter foam capable of preventing skin, acne, dirt, and care products from being sucked into the negative pressure generation assembly 60 by the negative pressure, which would cause wear or damage of the internal components. In addition, such filter foam is replaceable.

In view of the above, the present invention of the facial beautifying and care apparatus is able to achieve the expected objectives of use and to overcome the drawbacks of the prior arts. Therefore, the present invention is of novelty and an inventive step, complying with the patentability for an invention patent. Accordingly, this patent application is hereby filed according to the law in light of the grant of the patent right for the protection of the rights of the inventor.

What is claimed is:
1. A facial beautifying and care apparatus, comprising:
a beauty bar (1) having an air supply passage (A) arranged therein; the beauty bar (1) having a negative pressure connecting hole (132) and a conductive suction nozzle (15) communicating with the air supply passage (A) and arranged at two ends thereof respectively; the negative pressure connecting hole (132) having a first connection port (134) arranged at a lateral side thereof;
an electro muscle simulation generation module (20) arranged inside the beauty bar (1) and electrically connected to the first connection port (134);
an external negative pressure unit (6) arranged separately from the beauty bar (1); the external negative pressure unit (6) comprising a housing (61) and a negative pressure driving control module (62) installed inside the housing (61); the negative pressure driving control module (62) comprising an air supply tube assembly (66); the air supply tube assembly (66) having a negative pressure communicating hole (661) arranged on the housing (61); the external negative pressure unit (6) further comprising a second connection port (637);
a communicating tube (7) having two ends communicating with the negative pressure connecting hole (132) and the negative pressure communicating hole (661) respectively;
a conductive wire (8) having two ends connected to the first connecting port (134) and the second connecting port (637);
wherein through an operation of the negative pressure driving control module (62), the conductive suction nozzle (15) is able to generate negative pressure suction on facial skin, and a current is guided to flow outward via the electro muscle simulation generation module (20), thereby allowing the conductive suction nozzle (15) to simulate facial skin to generate adenosine tri-phosphate;
wherein the electro muscle simulation generation module (20) comprises a control assembly (21) and an electro muscle simulation transmission assembly (22); the control assembly (21) is electrically connected to the first connection port (134); the control assembly (21) comprises a circuit board (211) and a first switch button (212) installed on the circuit board (211) in order to turn on or off the electro muscle simulation transmission assembly (22) via a control on the first switch button (212);
wherein the electro muscle simulation transmission module assembly (22) comprises a wire (221); the conductive suction nozzle (15) comprises a connector (151) and a connector cap (155) connected thereto; the connector (151) includes a second connecting tube (152); one end of the wire (221) is electrically connected to the control assembly (21), and another end of the wire (221) is attached to the second connecting tube (152); and an ultrasonic generation module (30) arranged inside the beauty bar (1) and is electrically connected to the control assembly (21);

wherein the ultrasonic generation module (30) comprises a fixation plate (31) and a piezoelectric plate assembly (32) stacked onto the fixation plate (31); the fixation plate (31) and the piezoelectric plate assembly (32) are mounted onto the second connecting tube (152); the control assembly (21) further comprises a second switch button (213) installed on the circuit board (211), such that through an operation of the second switch button (213), an actuation of the ultrasonic generation module (30) is turned on or off.

2. The facial beautifying and care apparatus according to claim 1, wherein the electro muscle simulation transmission module assembly (22) further comprises a fixation member (222); an outer circumferential edge of the second connecting tube (152) includes a fastening portion (154); another end of the wire (221) is fastened corresponding to the fastening portion (154) via the fixation member (222).

3. The facial beautifying and care apparatus according to claim 2, wherein the connector (151) further comprises a hollow cylinder (153) extended from the second connecting tube (152) and communicating therewith; the connector cap (155) is mounted onto the hollow cylinder (153), and a center of the connector cap (155) includes an intake opening (156) communicating with the hollow cylinder (153) and the second connecting tube (152).

4. The facial beautifying and care apparatus according to claim 3, wherein the beauty bar (1) comprises a lower cap (13); the lower cap (13) includes an extension tube (131) formed thereon; the negative pressure connecting hole (132) is formed at a center of the extension tube (131); a first connecting tube (133) extends from a lower portion of the extension tube (131) correspondingly and communicates with the negative pressure connecting hole (132); a connecting tube (16) communicates with the first connecting tube (133) and the second connecting tube (152), thereby forming the air supply passage (A) inside the beauty bar (1).

5. The facial beautifying and care apparatus according to claim 1, wherein the electro muscle simulation generation module (20) further comprises an anti-false touch assembly (23); the anti-false touch assembly (23) comprises a capacitive sensing switch (231), a conductive spring (232) and a sensing portion (233); the capacitive sensing switch (231) is arranged on the circuit board (211); the conductive spring (232) is supported inside the beauty bar (1), and one end of the conductive spring (232) is arranged corresponding to the capacitive sensing switch (231); the sensing portion (233) is formed on a surface of the beauty bar (1) and is arranged corresponding to another end of the conductive spring (232).

6. The facial beautifying and care apparatus according to claim 1, further comprising a filter member (55); the connector (151) includes a hollow cylinder (153); the filter member (55) is arranged inside the hollow cylinder (153).

7. The facial beautifying and care apparatus according to claim 1, further comprising a waterproof gasket (17); the connector (151) includes a hollow cylinder (153) extended from and communicating with the second connecting tube (152); the waterproof gasket (17) is clamped between the connector cap (155) and the hollow cylinder (153).

8. The facial beautifying and care apparatus according to claim 1, further comprising a silicon cover (18); the beauty bar (1) comprises a bar member (10); the bar member (10) comprises a front housing (11), a rear housing (12), a lower cap (13) and an upper cap (14); the silicon cover (18) covers an exterior of the front housing (11) and the rear housing (12), and is connected to the lower cap (13) and the upper cap (14).

9. The facial beautifying and care apparatus according to claim 1, wherein the negative pressure driving control module (62) further comprises a controller (63), a negative pressure generation assembly (64) and a pressure relief assembly (65); the negative pressure generation assembly (64) and the pressure relief assembly (65) are electrically connected to the controller (63); the air supply tube assembly (66) communicates with the negative pressure generation assembly (64) and the pressure relief assembly (65).

10. The facial beautifying and care apparatus according to claim 9, wherein the controller (63) comprises a main circuit board (631); the main circuit board (631) includes a display panel (632), a continuous suction button (633), an intermittent suction release button (634), a negative pressure time control button (635), a pressure relief time control button (636) and two second connection ports (637) disposed thereon, and is electrically connected to the controller (63) via a power button (638).

11. A facial beautifying and care apparatus, comprising:
a beauty bar (1) having an air supply passage (A) arranged therein; the beauty bar (1) having a negative pressure connecting hole (132) and a conductive suction nozzle (15) communicating with the air supply passage (A) and arranged at two ends thereof respectively; the negative pressure connecting hole (132) having a first connection port (134) arranged at a lateral side thereof;

an electro muscle simulation generation module (20) arranged inside the beauty bar (1) and electrically connected to the first connection port (134);

an external negative pressure unit (6) arranged separately from the beauty bar (1); the external negative pressure unit (6) comprising a housing (61) and a negative pressure driving control module (62) installed inside the housing (61); the negative pressure driving control module (62) comprising an air supply tube assembly (66); the air supply tube assembly (66) having a negative pressure communicating hole (661) arranged on the housing (61); the external negative pressure unit (6) further comprising a second connection port (637);

a communicating tube (7) having two ends communicating with the negative pressure connecting hole (132) and the negative pressure communicating hole (661) respectively;

a conductive wire (8) having two ends connected to the first connecting port (134) and the second connecting port (637);

wherein through an operation of the negative pressure driving control module (62), the conductive suction nozzle (15) is able to generate negative pressure suction on facial skin, and a current is guided to flow outward via the electro muscle simulation generation module (20), thereby allowing the conductive suction nozzle (15) to simulate facial skin to generate adenosine tri-phosphate;

wherein the electro muscle simulation generation module (20) comprises a control assembly (21) and an electro muscle simulation transmission assembly (22); the control assembly (21) is electrically connected to the first connection port (134); the control assembly (21) comprises a circuit board (211) and a first switch button (212) installed on the circuit board (211) in order to turn on or off the electro muscle simulation transmission assembly (22) via a control on the first switch button (212);

wherein the electro muscle simulation transmission module assembly (22) comprises a wire (221); the conductive suction nozzle (15) comprises a connector (151) and a connector cap (155) connected thereto; the connector (151) includes a second connecting tube (152); one end of the wire (221) is electrically connected to the control assembly (21), and another end of the wire (221) is attached to the second connecting tube (152); and a light wave generation module (40) comprising a light emitting assembly (41) and a light shield (42); wherein the light emitting assembly (41) is arranged inside the beauty bar (1) and is electrically connected to the control assembly (21); the beauty bar (1) comprises an upper cap (14); the upper cap (14) comprises a shield disk (141); the light shield (42) covers onto an exterior of the shield disk (141); the control assembly (21) further comprises a third switch button (214) installed on the circuit board (211), such that through an operation of the third switch button (214), an actuation of the light wave generation module (4) is turned on or off.

12. The facial beautifying and care apparatus according to claim 11, wherein the light emitting assembly (41) comprises a substrate (411) and a plurality of light emitting diodes (412) disposed on the substrate (411); the shield disk (141) includes a plurality of conical light cups (143), and each of the conical light cups (143) is arranged corresponding to each one of the light emitting diodes (412) respectively.

13. A facial beautifying and care apparatus, comprising:
a beauty bar (1) having an air supply passage (A) arranged therein; the beauty bar (1) having a negative pressure connecting hole (132) and a conductive suction nozzle (15) communicating with the air supply passage (A) and arranged at two ends thereof respectively; the negative pressure connecting hole (132) having a first connection port (134) arranged at a lateral side thereof;
an electro muscle simulation generation module (20) arranged inside the beauty bar (1) and electrically connected to the first connection port (134);
an external negative pressure unit (6) arranged separately from the beauty bar (1);
the external negative pressure unit (6) comprising a housing (61) and a negative pressure driving control module (62) installed inside the housing (61); the negative pressure driving control module (62) comprising an air supply tube assembly (66); the air supply tube assembly (66) having a negative pressure communicating hole (661) arranged on the housing (61); the external negative pressure unit (6) further comprising a second connection port (637);
a communicating tube (7) having two ends communicating with the negative pressure connecting hole (132) and the negative pressure communicating hole (661) respectively;
a conductive wire (8) having two ends connected to the first connecting port (134) and the second connecting port (637);
wherein through an operation of the negative pressure driving control module (62), the conductive suction nozzle (15) is able to generate negative pressure suction on facial skin, and a current is guided to flow outward via the electro muscle simulation generation module (20), thereby allowing the conductive suction nozzle (15) to simulate facial skin to generate adenosine tri-phosphate;
wherein the electro muscle simulation generation module (20) comprises a control assembly (21) and an electro muscle simulation transmission assembly (22); the control assembly (21) is electrically connected to the first connection port (134); the control assembly (21) comprises a circuit board (211) and a first switch button (212) installed on the circuit board (211) in order to turn on or off the electro muscle simulation transmission assembly (22) via a control on the first switch button (212);
wherein the electro muscle simulation transmission module assembly (22) comprises a wire (221); the conductive suction nozzle (15) comprises a connector (151) and a connector cap (155) connected thereto; the connector (151) includes a second connecting tube (152); one end of the wire (221) is electrically connected to the control assembly (21), and another end of the wire (221) is attached to the second connecting tube (152); and
a negative ion generation module (50) arranged inside the beauty bar (1) and electrically connected to the control assembly (21); wherein the negative ion generation module (50) comprises a negative ion generator (51) and a negative ion wire (52) connected to the negative ion generator (51); the beauty bar (1) comprises an upper cap (14); the upper cap (14) comprises a shield disk (141); the shield disk (14) includes a negative ion output hole (144) formed thereon; the negative ion wire (52) extends into the negative ion output hole (144).

\* \* \* \* \*